(12) United States Patent
Mathur

(10) Patent No.: US 8,556,891 B2
(45) Date of Patent: Oct. 15, 2013

(54) VARIABLE-OUTPUT RADIOFREQUENCY ABLATION POWER SUPPLY

(75) Inventor: Charu P. Mathur, San Diego, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 871 days.

(21) Appl. No.: 12/716,893

(22) Filed: Mar. 3, 2010

(65) Prior Publication Data
US 2011/0218526 A1 Sep. 8, 2011

(51) Int. Cl.
*A61B 18/14* (2006.01)
(52) U.S. Cl.
USPC .......................................................... 606/34
(58) Field of Classification Search
USPC ............................... 606/27, 34, 41
See application file for complete search history.

(56) References Cited

U.S. PATENT DOCUMENTS

| | | | | |
|---|---|---|---|---|
| 4,051,855 A | * | 10/1977 | Schneiderman | 606/42 |
| 4,559,943 A | * | 12/1985 | Bowers | 606/37 |
| 4,860,744 A | * | 8/1989 | Johnson et al. | 606/31 |
| 5,334,193 A | * | 8/1994 | Nardella | 606/41 |
| 5,599,345 A | * | 2/1997 | Edwards et al. | 606/41 |
| 5,769,847 A | * | 6/1998 | Panescu et al. | 606/42 |
| 5,773,799 A | * | 6/1998 | Maxfield et al. | 219/661 |
| 5,971,980 A | * | 10/1999 | Sherman | 606/34 |
| 6,132,426 A | * | 10/2000 | Kroll | 606/41 |
| 6,142,992 A | | 11/2000 | Cheng et al. | |
| 6,329,727 B1 | | 12/2001 | Traveis et al. | |
| 6,461,351 B1 | * | 10/2002 | Woodruff et al. | 606/32 |
| 6,558,378 B2 | * | 5/2003 | Sherman et al. | 606/34 |
| 2003/0195501 A1 | | 10/2003 | Sherman et al. | |
| 2005/0143725 A1 | * | 6/2005 | Daners et al. | 606/39 |
| 2008/0067987 A1 | | 3/2008 | Tung et al. | |

FOREIGN PATENT DOCUMENTS

EP 2080482 A1 7/2009
WO 2008102154 A2 8/2008

\* cited by examiner

*Primary Examiner* — Michael Peffley
*Assistant Examiner* — Daniel Fowler
(74) *Attorney, Agent, or Firm* — Christopher & Weisberg, P.A.

(57) ABSTRACT

A medical system is provided, including an ablation system having at least one ablation element and a sensor, a generator operable to deliver radiofrequency ablation energy to the ablation element. A power supply defines a duty cycle and provides a voltage to the generator, and the power supply has a duty cycle modulator and an amplitude modulator. A processor is connected to the power supply, the generator, and the sensor. The processor obtains a feedback signal from the sensor, and adjusts the duty cycle modulator and the amplitude modulator according to the feedback signal.

16 Claims, 7 Drawing Sheets

VARIABLE-OUTPUT RADIOFREQUENCY ABLATION POWER SUPPLY

CROSS-REFERENCE TO RELATED APPLICATION

N/A.

STATEMENT REGARDING FEDERALLY SPONSORED RESEARCH OR DEVELOPMENT

N/A.

FIELD OF THE INVENTION

The present invention relates generally to medical systems and methods of use thereof, and more particularly to an ablation system having a variable output power supply.

BACKGROUND OF THE INVENTION

Numerous procedures involving catheters and other minimally invasive devices may be performed for a wide variety of treatments, such as ablation, angioplasty, dilation or other similar therapies. For example, there are many variations of cardiac arrhythmias with different causes, including atrial fibrillation, generally involving irregularities in the transmission of electrical impulses through the heart. To treat cardiac arrhythmias or irregular heartbeats, physicians often employ specialized ablation catheters to gain access to interior regions of a patient's body. Such catheters include tip electrodes or other ablating elements to create ablation lesions that physiologically alter the ablated tissue without removal thereof, disrupting or blocking electrical pathways through the targeted tissue. In the treatment of cardiac arrhythmias, a specific area of cardiac tissue, such as for example atrial rotors, having aberrant electrically conductive pathways with erratic electrical impulses is initially localized. A medical practitioner (such as a physician) may direct a catheter through a body passage including for example a blood vessel into the interior region of the heart that is to be treated. Subsequently, the ablating portion of the selected device is placed near the targeted cardiac tissue to be ablated, such as for example a pulmonary vein ostium or atrium.

An ablation procedure may involve creating one or more lesions in order to electrically isolate tissue believed to be the source of an arrhythmia. During the course of such a procedure, a physician may perform, for example, radio-frequency (RF) ablation which includes diagnosing aberrant tissue and destroying it with local administration of radio frequency energy. RF ablation may be performed by provide an RF electrical signal to one or more electrodes in contact with the tissue to be ablated, and the energy resistively heats the surrounding tissue. Eventually, the heating process destroys the selected cells surrounding the electrodes, and the ablation is completed.

Local conditions near the selected ablation site may change during delivery of RF ablation energy, for example due to fluid flow of blood and possibly saline solution. These fluids may be electrically conductive, and local fluid flow during ablation energy delivery to the electrodes may alter the electrodes' impedance. Depending upon the specific configuration of the medical system, the patient's anatomy and fluids near the ablation electrodes, the impedance characteristics during an ablation procedure may change by an amount ranging from a fraction of an ohm to more than 200 ohms.

This significant variation in local conditions may lead to consequences such as for example some undesirable tissue ablation, local generation of steam, or other overheating. Given variations in anatomy and the possibility of concurrent changes in the tissue treatment environment and the potential effect such variation may have on a therapeutic procedure, it is therefore desirable to provide a safe and effective medical ablation system having a feedback mechanism which automatically and continuously adjusts the ablation energy to ablate the desired tissue to be treated. It is also desirable to provide an ablation system and method for controlling the surface area and depth of ablation, and which automatically discontinues ablation once the desired treatment has been achieved.

SUMMARY OF THE INVENTION

The present invention advantageously provides a medical system for treating patients by ablating pre-selected tissue through the use of a generator, a catheter with at least one ablation element, a patient return electrode, and a feedback system to verify and monitor the electrical connection between the generator and the patient return electrode, as well as contact of the patient return electrode with the patient.

In particular, a medical system is provided, including a catheter having an ablation element and a sensor; a generator connected to the catheter, the generator being operable to deliver radio frequency ablation energy to the ablation element; a power supply defining a duty cycle and providing a voltage to the generator, the power supply having a duty cycle modulator and an amplitude modulator; and a processor connected to the power supply, the generator, and the sensor; where the processor is operable to obtain a feedback signal from the sensor, and adjust the duty cycle modulator and the amplitude modulator according to the feedback signal.

A medical system is also provided, including a catheter having an ablation element and a sensor; a generator connected to the catheter, the generator being operable to deliver radiofrequency ablation energy to the ablation element; a power supply defining a duty cycle and providing a voltage to the generator; a proportional-integral-derivative controller operable to modulate the duty cycle; a variable resistance array of parallel resistors connected to the sensor, and a switch connected to each resistor; the variable resistance array being operable to modulate an amplitude of the voltage; a processor connected to the power supply, the generator, and the variable resistance array; where the processor is operable to obtain a feedback signal from the sensor, and adjust the duty cycle and the amplitude according to the feedback signal.

A method of treating a patient is provided, including providing an ablation system having a power supply, a generator, an ablation element, and a sensor; determining a desired parameter value; operating the power supply to define a duty cycle and an output voltage; placing the ablation element and sensor proximate to a treatment site; delivering electrical power from the power supply to the generator; delivering ablation energy from the generator to the ablation element; measuring a parameter with the sensor; comparing the measured parameter to the desired parameter value to determine a comparison value; and modulating the duty cycle and the output voltage to minimize the comparison value.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 6 is an illustration of another medical device in accordance with the principles of the present invention;

DETAILED DESCRIPTION OF THE INVENTION

Figure 1:
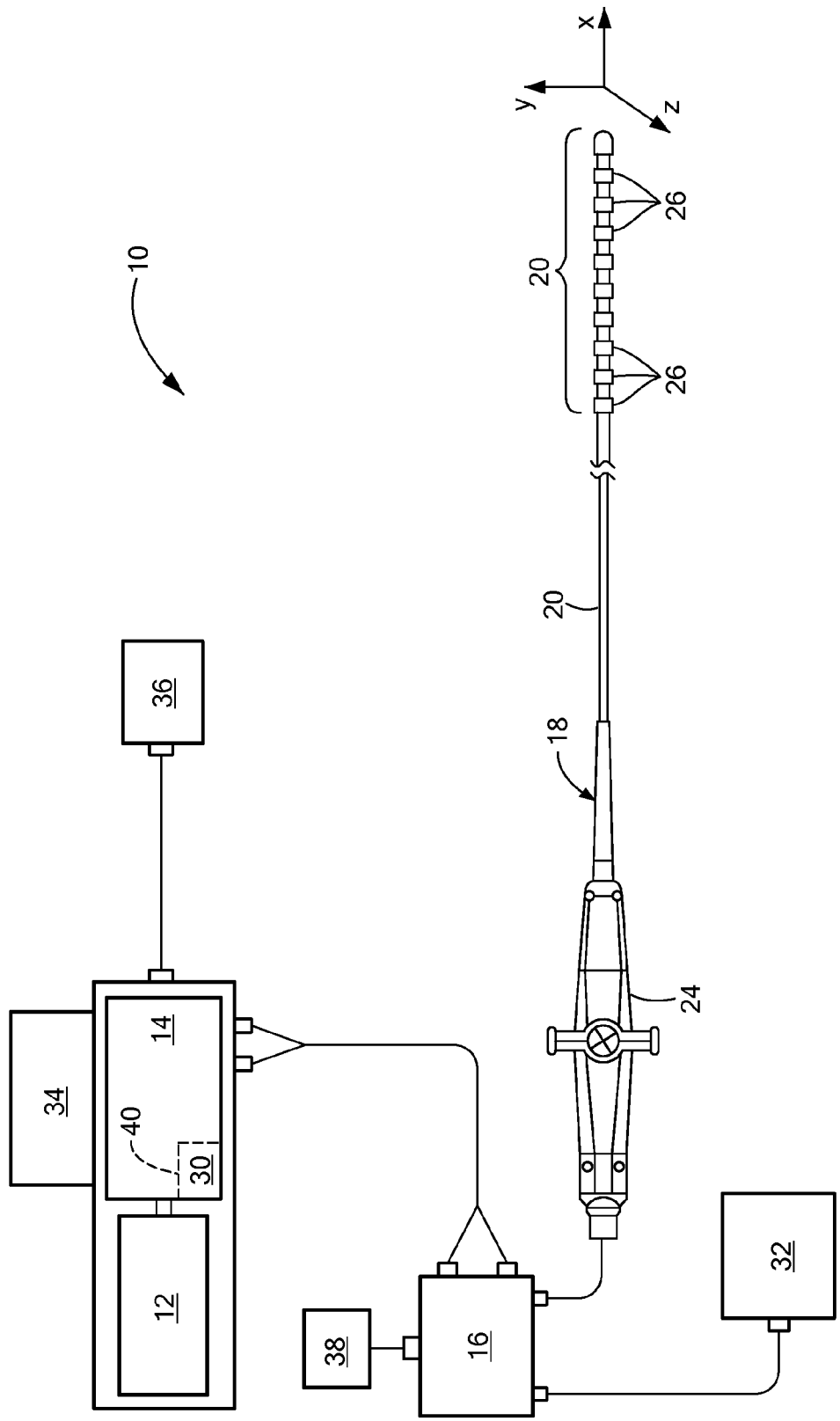
FIG. 1 is an illustration of a medical system in accordance with the principles of the present invention.

The present invention advantageously provides a medical system and method for treating patients by performing an ablation procedure in which a feedback mechanism can automatically and continuously adjust the ablation energy to safely and effectively ablate the desired tissue to be treated. In particular and as shown in FIG. 1, an ablation therapy system, generally designated at 10, is provided for treating unwanted tissue conditions, including for example atrial fibrillation or other arrhythmias. The ablation therapy system 10 may generally include a power supply 12 operably coupled to an electrical generator such as for example a radio-frequency ("RF") generator 14, an electrocardiogram ("ECG") unit 16 operably coupled to the RF generator 14, and a medical device 18.

The medical device 18 may include a catheter for performing various medical treatments, including for example an electrophysiology catheter which may be operably coupled to the RF generator 14 and the ECG unit 16. The medical device 18 may have a shape and dimensions to reach various treatments sites, such as intraluminal access to vascular anatomy, including for example transseptal access to the left atrium of a patient's heart for subsequent treatment or ablation. The medical device 18 may generally define an elongated, flexible catheter body 20 having a distal treatment assembly 22, as well as a handle assembly 24 at or near a proximal end of the catheter body 20.

The distal treatment assembly 22 may, for example, include one or more ablation elements such as electrodes 26 and one or more sensors such as thermocouples 28. Each electrode 26 may be electrically coupled to an output portion of the RF generator 14, and each thermocouple 28 may be electrically coupled to a feedback portion of the RF generator 14. Of course, the sensors may be of any suitable type, including for example an electrical conductivity sensor, a spectrometer, a pressure sensor, a fluid flow sensor, a pH sensor, and a thermal sensor.

Power supply 12 may accept an input voltage and produce an output voltage to the RF generator 14, which in turn delivers radiofrequency ablation energy to the ablation electrodes 26. The resulting thermal energy at the electrodes 26 may then be verified and continuously monitored by the thermocouples 28, which send feedback signals back to a processor 30 which is connected to the power supply 12, the generator 14, and the thermocouples 28.

A patient return electrode 32 may also be provided, and may include a conductive pad having a greater surface area than the electrodes 26. The patient return electrode 26 may be external to the patient, for example in contact with the patient's skin through an adhesive attachment to the back of the patient, and may be operably coupled to the ECG unit 16 and/or directly to the RF generator 14.

The ablation therapy system 10 may have one or more modes of operation, including for example: (i) bipolar ablation delivering ablation energy between at least two of the electrodes 26 of the treatment assembly 22 on the medical device 18 within a patient's body, (ii) monopolar ablation delivering ablation energy to one of the electrodes 26 of the distal treatment assembly 22 on the medical device 18 within a patient's body and through the patient return electrode 32 contacting a patient's skin, and (iii) a combination of the monopolar and bipolar modes.

The RF generator 14 may also include a user interface 34 which may include a display and/or a remote control 36, which enable a user to select parameters for desired mapping and/or ablation treatment. The user interface 34 may allow the user to select an energy delivery mode for treatment, such as for example, selection among the delivery of only monopolar energy, only bipolar energy, or a combination of the two. When in combination mode, the user interface 34 may also allow selection a power ratio of monopolar energy to bipolar energy, such as 1:1, 2:1, or 4:1. The RF generator 14 may offer a set of specific energy ratios by default, such that the user can select one of the established energy ratios, and/or the user interface can allow the user to enter a different custom energy ratio. The user interface 34 may also allow changing the energy mode when the catheter is changed, or when the medical device 18 is moved to a different location to ablate different tissue.

The ECG unit 16 may also have an ECG monitoring unit or display 38 to monitor and map signals detected by the electrodes 26 of the distal treatment assembly 22 of the medical device 18. The RF generator 14 and the ECG unit 16 may both be operably coupled to the medical device 18. The ECG unit 16 may be designed to electrically isolate itself and the display 38 from the signals generated by the RF generator 14, which may include isolation from large magnitude signals and electrical noise that may result from the RF generator 14.

Power supply 12 may be a switched-mode power supply with a buck converter which defines a duty cycle, and may have feedback mechanisms to adjust the output voltage, including for example a duty cycle modulator and an amplitude modulator. Depending on the mode of operation at the moment, the power supply 12 determines a desired parameter for local conditions near the ablation elements. This desired parameter may for example be a desired temperature, and may be called the "setpoint."

The feedback mechanisms obtain feedback signals from sensors near the ablation elements, compare the feedback signals to the setpoint, and calculate the difference between the desired setpoint and the feedback signals, to arrive at a comparison value.

The duty cycle modulator feedback mechanism may be a proportional-integral-derivative (PID) controller 40 which uses a processor algorithm to minimize the comparison value by adjusting the power supply duty cycle. The PID controller 40 may take the form of a subset of the circuitry of processor 30, or any other suitable arrangement, including for example a software subroutine or a separate controller unit. In operation, the PID controller 40 calculates a proportional term based on the current comparison value, an integral term based on the sum of recent comparison values, and a derivative value term based on the rate at which the comparison value has changed. The power supply duty cycle is then modulated by the PID controller 40, to adjust the power supply output voltage to the RF generator 14 and control the ablation.

Figure 2:
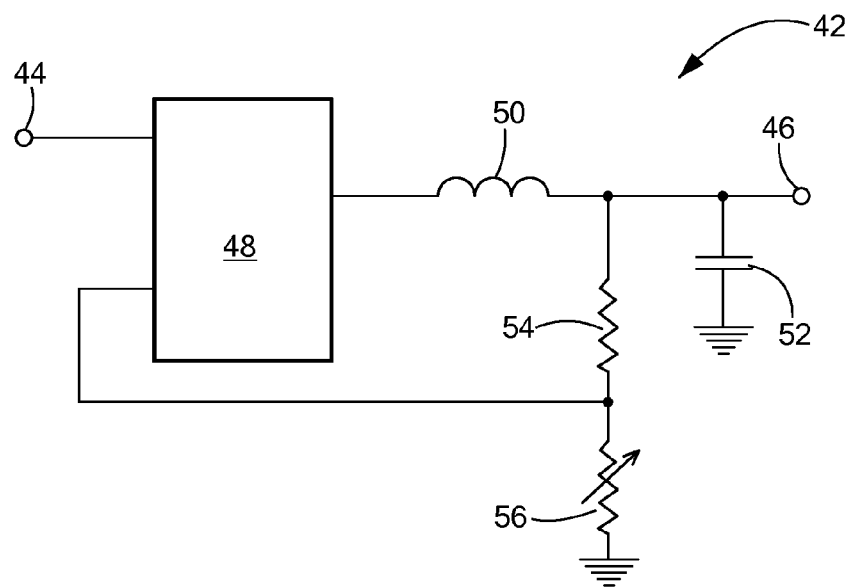
FIG. 2 is an illustration of a circuit diagram for a variable-output power supply for the medical system of FIG. 1, in accordance with the principles of the present invention.

FIG. 2 depicts a circuit diagram of a variable-output power supply 12 for use in a medical ablation system shown in FIG. 1. Power supply 12 may include a buck convertor 42, having an input voltage 44 and producing an output voltage 46 based on feedback signals from the sensors (such as thermocouples 28 for example), and then adjusting the duty cycle modulator and the amplitude modulator according to the feedback signals. The buck convertor 42 may incorporate a regulator or processor 48 in the form of an integrated circuit, such as for example the commercially available integrated circuit LTC 1775. The specific example of a buck convertor 42 performs a variable step-down conversion of a direct current (DC) input voltage to a DC output voltage. The input voltage 44 may be selected among a range of suitable amounts, such as for example a voltage equal to or less than 20 volts DC, including a more specific example of approximately 4.7 volts. The processor 48 may be combined with several components such as for example an inductor 50, a capacitor 52, a resistor 54, and a variable resistance 56.

Figure 3:
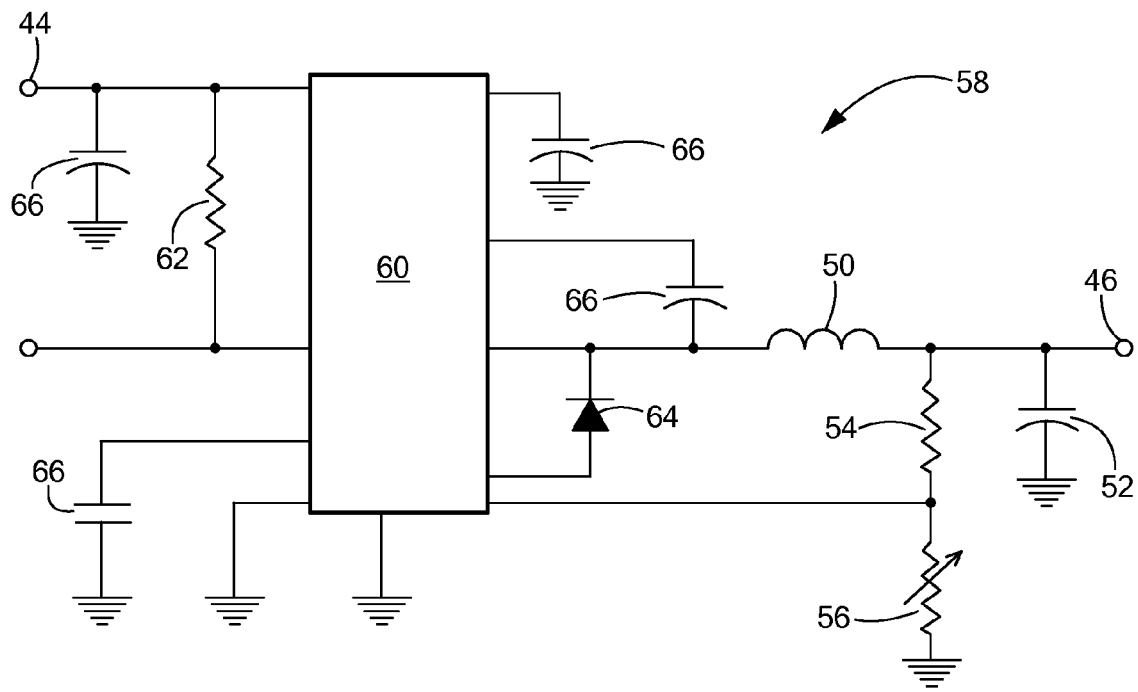
FIG. 3 is an illustration of a circuit diagram for a variable-output power supply having additional components in accordance with the principles of the present invention.

FIG. 3 depicts a more specific example of a variable-output power supply having a buck convertor 58 with a PID controller to modulate the duty cycle, in which the input voltage 44, the output voltage 46, the inductor 50, the capacitor 52, the resistor 54, and the variable resistance 56 are indicated by the same reference numerals as those in FIG. 2. A regulator or processor 60 is more complex than the processor 48 of FIG. 2, and additional components are added including for example an additional resistor 62, a diode 64, and capacitors 66. Additional resistor 62 may for example serve to raise the input voltage to the processor 60 greater than input voltage 44, which may improve overall efficiency of the power source. Diode 64 may be a conventional diode, or as a more specific example may be a Schottky diode, and may operate to recharge a capacitor which powers a field-effect transistor (FET) inside variable resistance 56. Capacitors 66 may assist in handling root-mean-square (RMS) current at the input, and avoiding ripple at the output 46.

Figure 4:
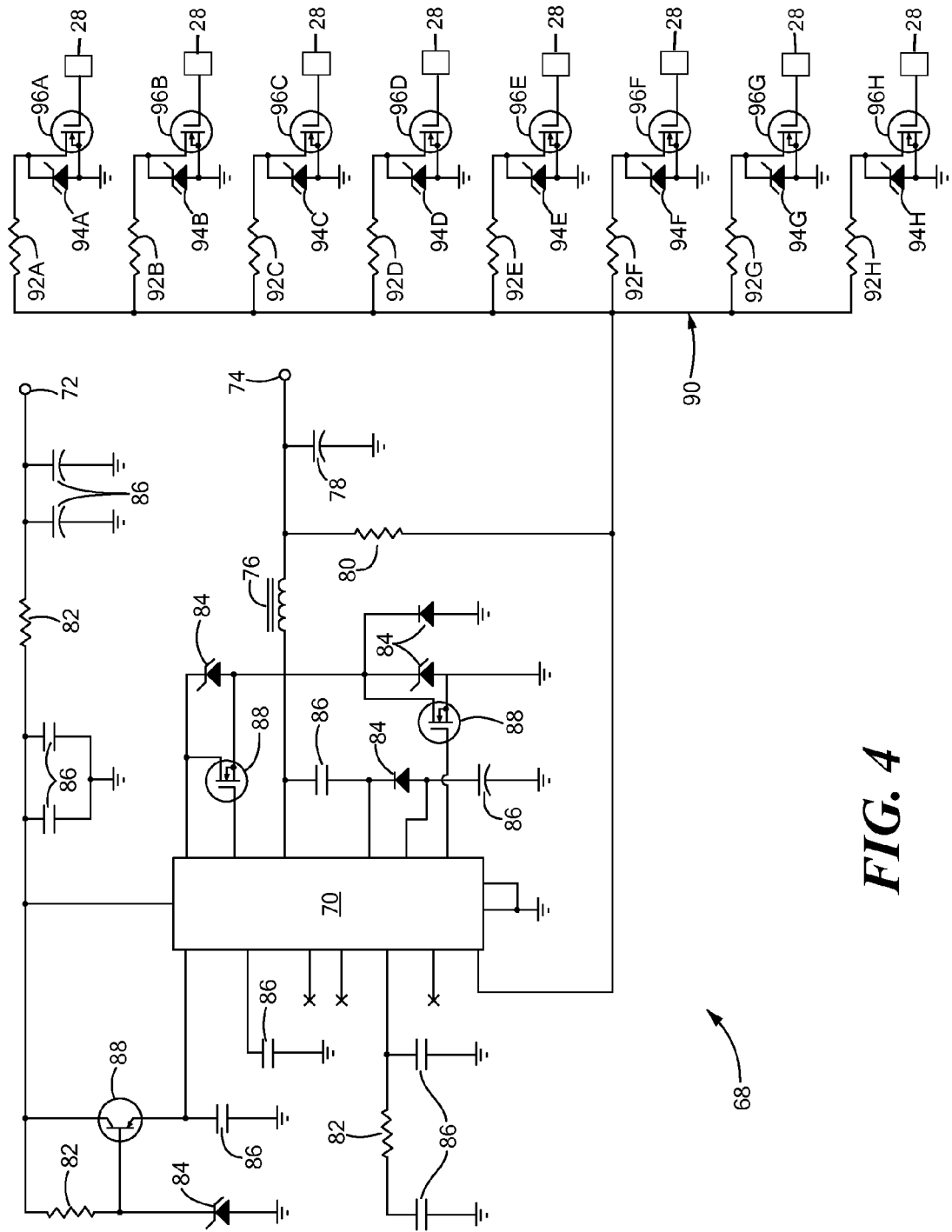
FIG. 4 is an illustration of a circuit diagram for a variable-output power supply having additional components in accordance with the principles of the present invention.

FIG. 4 shows a variable-output power supply 68 with even more detail, and which adds a variable resistance array for amplitude modulation. For example, processor 70 accepts an input voltage 72 and produces an output voltage 74, based on feedback signals from the sensors for example thermocouples 28, and then adjusts the duty cycle modulator as well as the amplitude modulator according to the feedback signals. In particular, an inductor 76, a capacitor 78, and a resistor 80 perform in a similar manner as those in FIG. 2, and circuit includes additional components such as for example resistors 82, diodes 84, capacitors 86, and transistors 88. These additional components may be selected to have a variety of suitable characteristics. More specifically, the specific type of transistors may be metal-oxide semiconductor field-effect transistors.

The amplitude modulator feedback mechanism may be a variable resistance array 90, operably coupled between the processor 70 and the thermocouples 28. The variable resistance array 90 has a plurality of parallel resistors 92A-H, each of which is coupled with a FET that combines the features of a diode 94A-H and a transistor 96A-H. Based on the feedback signals from the thermocouples 28, the processor 30 may activate one of the transistors 96 to allow current to flow through the corresponding resistor 94 and thus modulate the amplitude of the duty cycle.

In the specific example shown in FIG. 4, eight parallel resistors 92A-H are illustrated, though any suitable number of parallel resistors may be selected. Also, each parallel resistor 92 may be selected to have a different resistance, and in a specific example they may have the following sequence of resistances in ohms: 1024k, 512k, 256k, 128k, 64k, 32k, 16k, and 8k. Of course, any suitable variety of parallel resistances may be chosen.

Figure 5:
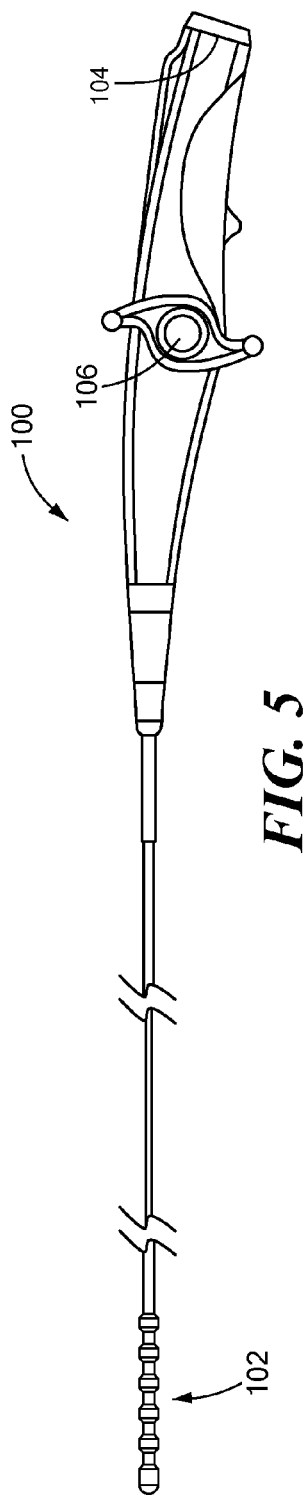
FIG. 5 is an illustration of a medical device in accordance with the principles of the present invention.
Figure 6:
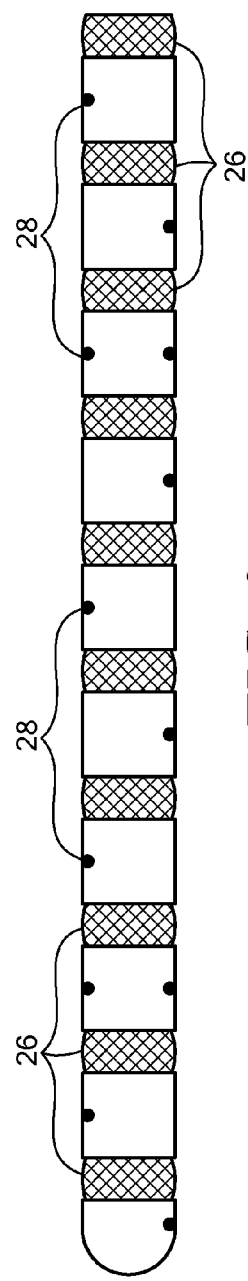
FIG. 6 is an illustration of the treatment assembly of FIG. 5, in accordance with the principles of the present invention.

Now referring to FIGS. 5-11, some exemplary medical devices are depicted. In particular, FIG. 5 shows an ablation catheter 100 having a distal treatment assembly 102 in which the electrodes 26 have a linear configuration. The distal treatment assembly 102 may be used for bipolar ablation between the electrodes 26 of the distal treatment assembly 102, or for monopolar ablation between one electrode 26 and a patient return electrode 32, or a combination of bipolar ablation and monopolar ablation. A proximal handle 104 has a rotational actuator 106 for manipulating, bending, steering and/or reshaping the distal treatment assembly 102 into various desired shapes, curves, etc. FIG. 6 shows the distal treatment assembly 102 in greater detail, including the electrodes 26 and the thermocouples 28.

Figure 7:
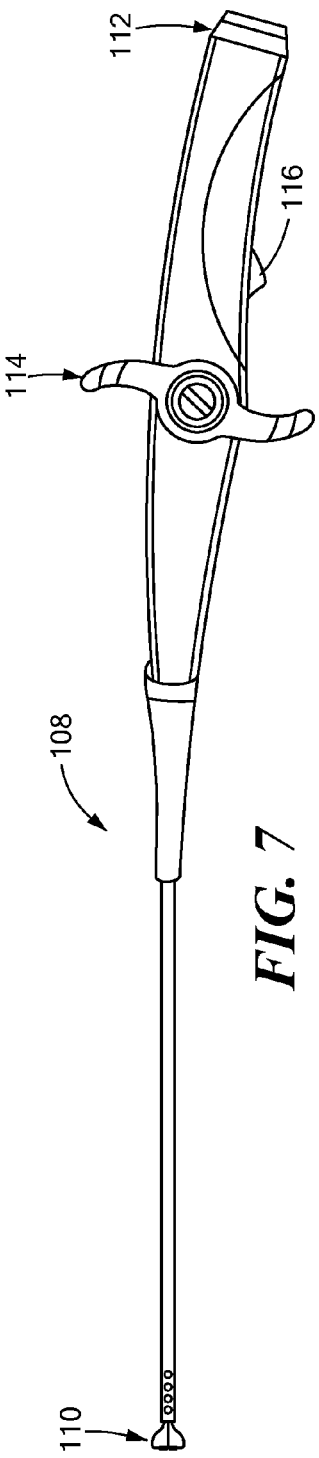
Figure 8:
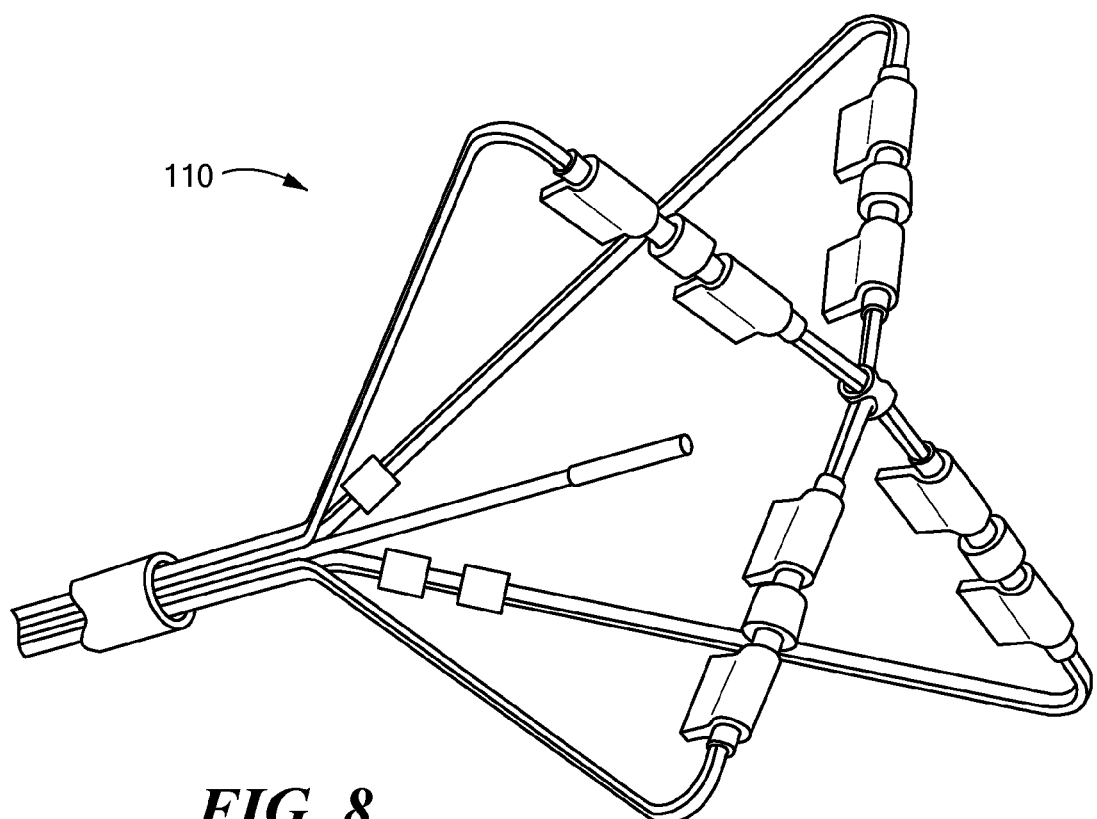
FIG. 8 is a perspective illustration of a treatment assembly for the medical device of FIG. 6, in accordance with the principles of the present invention.
Figure 9:
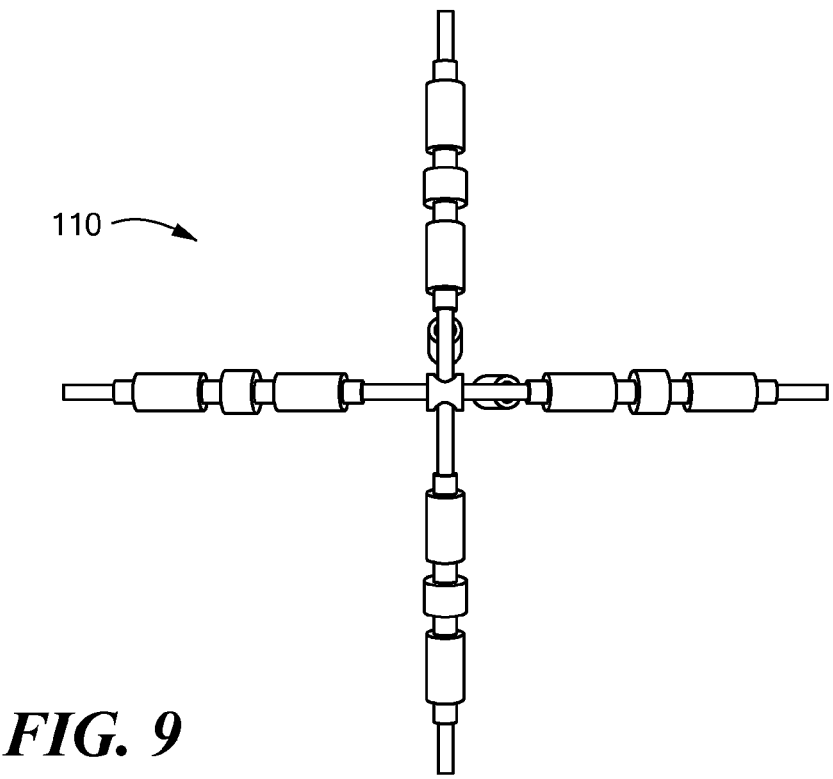
FIG. 9 is an illustration of the treatment assembly of FIG. 8, in accordance with the principles of the present invention.

FIGS. 7-9 show an ablation catheter 108 with a distal treatment assembly 110 in which the electrodes have a planar configuration. Similar to the ablation catheter 100, the distal treatment assembly 110 may be used for bipolar ablation, monopolar ablation, or a combination thereof. A proximal handle 112 has a rotational actuator 114 for manipulating a distal portion of the ablation catheter 108, and a linear actuator 116. The linear actuator 116 can advance the distal treatment assembly 110 distally beyond a catheter shaft, and retract the distal treatment assembly 110 proximally inside the catheter shaft. When the distal treatment assembly 110 is advanced distally, it may resiliently expand from a compressed arrangement inside the catheter shaft to the deployed arrangement shown in FIGS. 8 and 9.

Figure 10:
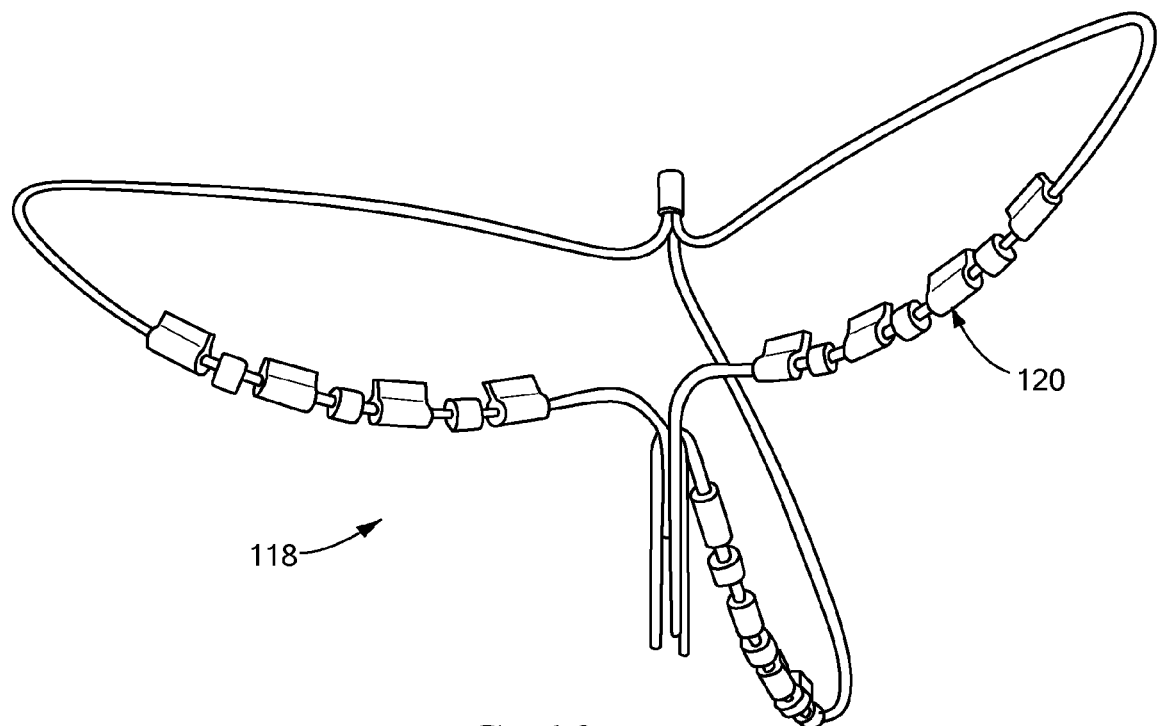
FIG. 10 is an illustration of another treatment assembly in accordance with the principles of the present invention.

FIG. 10 shows a catheter 118 which has a distal treatment assembly 120 having a resilient framework in which the electrodes have a proximally-directed configuration, which may for example be used for transseptal treatments of a patient's heart.

Figure 11:
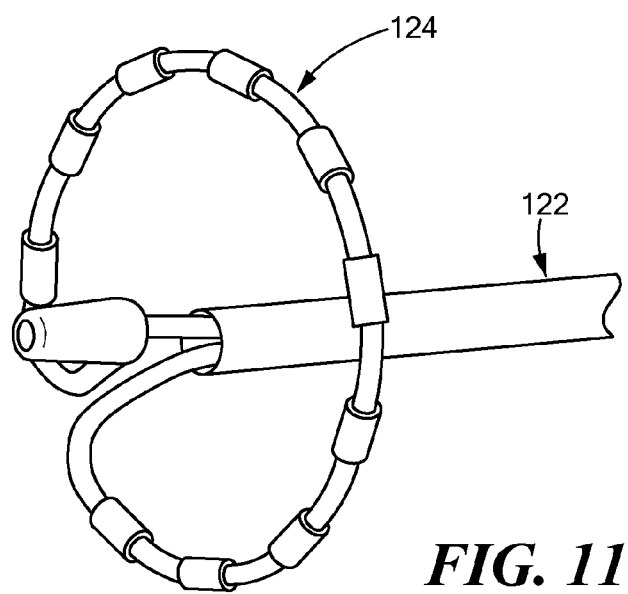
FIG. 11 is an illustration of an additional treatment assembly in accordance with the principles of the present invention.

FIG. 11 shows a catheter 122 which has a distal treatment assembly 124 in which the electrodes have an adjustable linear, planar, or spiral configuration.

Accordingly, the medical device 18 may be used to investigate and treat aberrant electrical impulses or signals in a selected tissue region, such as in the heart. Primarily, the distal treatment assembly 22 may be advanced through the patient's vasculature via the femoral artery over a previously inserted guidewire. The distal treatment assembly 22 may then be advanced into the right atrium and into proximity of a pulmonary vein, for example.

Figure 12:
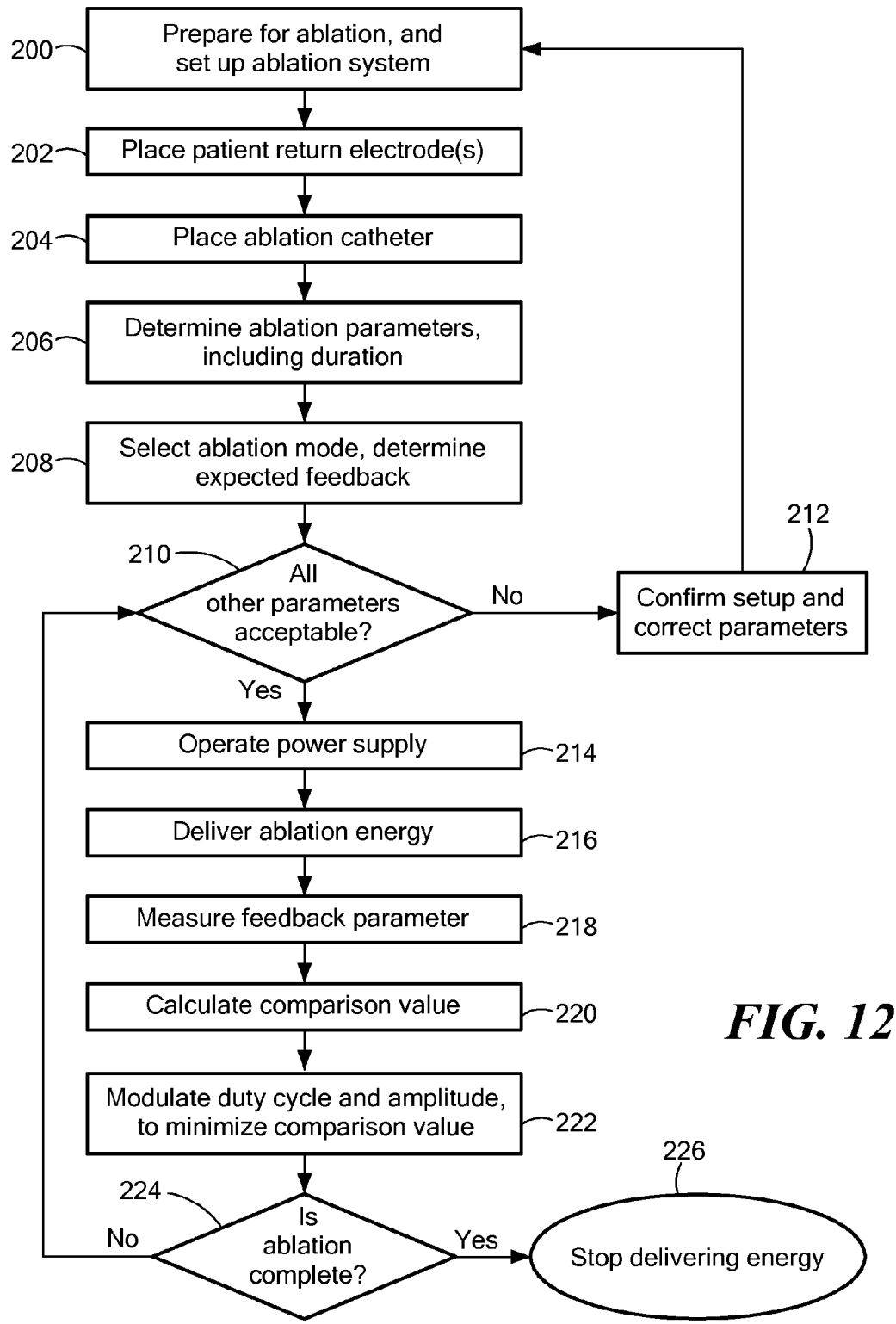
FIG. 12 is an illustration of a flow diagram in accordance with the principles of the present invention.

In an exemplary use of the present system as illustrated in the flow diagram of FIG. 12, the medical system is first prepared for ablation, and the ablation system is set up (step 200). One or more patient return electrodes are placed (step 202), and the ablation catheter is placed so that a distal treatment assembly having electrodes and sensors is in the desired position for treatment (step 204). Various ablation parameters are determined, including the intended duration of ablation (step 206). The desired ablation mode is selected, for example monopolar ablation, bipolar ablation, or a specific combination thereof, and the expected feedback parameter value is determined (step 208). For example, if the sensors are thermal sensors, then an expected feedback parameter value may be selected at a temperature which is below a fluid boiling temperature under local conditions, which may be 100 degrees Celsius.

If all parameters are not acceptable (step 210), then the setup and parameters are evaluated and corrected (step 212). If all parameters are acceptable, then delivery of ablation energy may commence. A power supply is operated, defining a duty cycle providing an output voltage to a generator (step 214), and ablation energy is delivered from the generator to the electrodes (step 216).

During ablation, a feedback parameter is continuously measured (step 218), and the measured feedback parameter is compared to the expected feedback parameter to determine a comparison value (step 220). The duty cycle and amplitude are independently modulated to minimize the comparison value (step 222). When ablation is complete (step 224), the ablation system stops delivering energy (step 224).

While examples and illustrations of particular medical system configurations have been provided, it is understood that various arrangements, shapes, configurations, and/or dimensions may be included in the medical device of the present invention, including but not limited to those illustrated and described herein. Also, though monopolar and bipolar RF ablation energy may be the selected forms of energy to pass through the electrodes of the medical device, other forms of ablation energy may be additionally or alternatively emitted from the treatment assembly, including electrical energy, magnetic energy, microwave energy, thermal energy (including heat and cryogenic energy) and combinations thereof. Moreover, other forms of energy that may be applied can include acoustic energy, sound energy, chemical energy, photonic energy, mechanical energy, physical energy, radiation energy and a combination thereof.

It should be understood that an unlimited number of configurations for the present invention could be realized. The foregoing discussion describes merely exemplary embodiments illustrating the principles of the present invention, the scope of which is recited in the following claims. In addition, unless otherwise stated, all of the accompanying drawings are not to scale. Those skilled in the art will readily recognize from the description, claims, and drawings that numerous changes and modifications can be made without departing from the spirit and scope of the invention.

What is claimed is:

1. A medical system, comprising:
    a catheter having an ablation element and a sensor;
    a radiofrequency generator connected to the ablation element;
    a power supply defining a duty cycle and providing a voltage to the generator, the power supply having a duty cycle modulator and an amplitude modulator; and
    a processor connected to the power supply, the generator, and the sensor, the amplitude modulator including a variable resistance connected between the sensor and the processor, the variable resistance including a plurality of parallel resistors, each parallel resistor having a different ohmic resistance and being connected to a diode and a transistor;
    the processor being operable to obtain a feedback signal from the sensor, and adjust the duty cycle modulator and the amplitude modulator according to the feedback signal, the processor allowing electrical current through one or more of the parallel resistors by selecting and activating the corresponding transistor in order to adjust the amplitude modulator.

2. The medical system of claim 1, wherein the processor is operable to adjust the variable resistance corresponding to the feedback signal.

3. The medical system of claim 1, wherein each transistor is a metal-oxide semiconductor field-effect transistor.

4. The medical system of claim 1, wherein the duty cycle modulator further comprises a proportional-integral-derivative controller.

5. The medical system of claim 1, wherein the power supply further comprises a buck convertor.

6. The medical system of claim 1, wherein the sensor is selected from the group consisting of a pH sensor, an electrical conductivity sensor, a spectrometer, a pressure sensor, a fluid flow sensor, and a thermal sensor.

7. The medical system of claim 1, wherein the ablation element is at least one electrode.

8. The medical system of claim 1, wherein the sensor is at least one thermocouple, and the feedback signal represents a temperature.

9. The medical system of claim 1, wherein the sensor is proximate to the ablation element.

10. A method of treating a patient, comprising:
    providing an ablation system having
        a generator;
        a power supply defining a duty cycle and providing a voltage to the generator, the power supply having a duty cycle modulator and an amplitude modulator;
        an ablation element;
        a sensor; and
        a processor connected to the power supply, the generator, and the sensor, the amplitude modulator including a variable resistance connected between the sensor and the processor, the variable resistance including a plurality of parallel resistors, each parallel resistor having a different ohmic resistance and being connected to a diode and a transistor, the processor being operable to obtain a feedback signal from the sensor and adjust the duty cycle modulator and the amplitude modulator according to the feedback signal, the processor allowing electrical current through one or more of the parallel resistors by selecting and activating the corresponding transistor in order to adjust the amplitude modulator;
    determining a desired parameter value;
    operating the power supply to define a duty cycle and an output voltage;
    placing the ablation element and sensor proximate to a treatment site;
    delivering electrical power from the power supply to the generator;
    delivering ablation energy from the generator to the ablation element;
    measuring a parameter with the sensor;
    comparing the measured parameter to the desired parameter value to determine a comparison value; and
    modulating the duty cycle and the output voltage to minimize the comparison value.

11. The method of claim 10, wherein the ablation energy is RF, and the desired parameter value is a temperature.

12. The method of claim 10, wherein operating the power supply further comprises providing an input voltage to the power supply, and the electrical power is selectable within a range of approximately 5% to 100% of the input voltage.

13. The method of claim 10, wherein modulating the duty cycle and the output voltage is performed continuously while delivering ablation energy from the generator to the ablation element.

14. The method of claim 10, wherein modulating the duty cycle and the output voltage reduces an amount of electrical noise produced by the ablation system and increases an electrical efficiency of the ablation system.

15. The method of claim 10, wherein modulating the output voltage to minimize the comparison value further comprises increasing the amplitude of the voltage when the signal is less than the desired parameter value, and decreasing the amplitude of the voltage when the signal is greater than the desired parameter value.

16. The method of claim 15, wherein providing an ablation system further comprises providing a variable resistance array of parallel resistors; and modulating the output voltage to minimize the comparison value further comprises selecting and allowing electrical current through one of the resistors.

* * * * *